United States Patent
Benson et al.

(10) Patent No.: US 11,850,301 B2
(45) Date of Patent: Dec. 26, 2023

(54) ORAL CARE COMPOSITION

(71) Applicant: Church & Dwight Co., Inc., Princeton, NJ (US)

(72) Inventors: Jennifer Benson, Newtown, PA (US); Elena Petrovicova, Princeton, NJ (US); William D. Platt, Lumberton, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 689 days.

(21) Appl. No.: 16/615,635

(22) PCT Filed: May 25, 2018

(86) PCT No.: PCT/IB2018/053759
§ 371 (c)(1),
(2) Date: Nov. 21, 2019

(87) PCT Pub. No.: WO2018/215994
PCT Pub. Date: Nov. 29, 2018

(65) Prior Publication Data
US 2020/0170942 A1   Jun. 4, 2020

Related U.S. Application Data

(60) Provisional application No. 62/511,715, filed on May 26, 2017.

(51) Int. Cl.
| | |
|---|---|
| *A61K 9/00* | (2006.01) |
| *A61K 31/045* | (2006.01) |
| *A61K 31/245* | (2006.01) |
| *A61K 47/10* | (2017.01) |
| *A61K 47/26* | (2006.01) |
| *A61K 47/32* | (2006.01) |
| *A61K 47/38* | (2006.01) |
| *A61K 47/44* | (2017.01) |
| *A61K 47/46* | (2006.01) |

(52) U.S. Cl.
CPC .......... *A61K 9/0053* (2013.01); *A61K 31/045* (2013.01); *A61K 31/245* (2013.01); *A61K 47/10* (2013.01); *A61K 47/26* (2013.01); *A61K 47/32* (2013.01); *A61K 47/38* (2013.01); *A61K 47/44* (2013.01); *A61K 47/46* (2013.01)

(58) Field of Classification Search
CPC .. A61K 9/0053; A61K 31/045; A61K 31/245; A61K 47/10; A61K 47/26; A61K 47/32; A61K 47/38; A61K 47/44; A61K 47/46
See application file for complete search history.

(56) References Cited

U.S. PATENT DOCUMENTS

| | | | |
|---|---|---|---|
| 6,074,674 A | 6/2000 | Kluemper et al. | |
| 6,589,562 B1 | 7/2003 | Shefer et al. | |
| 7,803,392 B2 | 9/2010 | Mumper et al. | |
| 8,173,152 B2 | 5/2012 | Crowley et al. | |
| 2003/0147956 A1 | 8/2003 | Shefer et al. | |
| 2004/0018250 A1 | 1/2004 | Ceccoli et al. | |
| 2004/0101494 A1 | 5/2004 | Scott et al. | |
| 2006/0263393 A1* | 11/2006 | Demopulos | A61P 25/00 514/355 |
| 2006/0292520 A1* | 12/2006 | Dillon | A61C 19/063 433/80 |
| 2009/0263467 A1* | 10/2009 | Joshi | A61K 31/4178 424/94.1 |
| 2017/0136078 A1 | 5/2017 | Li et al. | |

FOREIGN PATENT DOCUMENTS

| | | | |
|---|---|---|---|
| CN | 102198126 | | 9/2011 |
| WO | WO 2001/058416 | * | 8/2001 |
| WO | 2002/004004 | | 1/2002 |
| WO | WO 2011/027216 | * | 3/2011 |

* cited by examiner

*Primary Examiner* — Genevieve S Alley
(74) *Attorney, Agent, or Firm* — Church & Dwight Co., Inc.

(57) ABSTRACT

The present invention provides an oral care composition which includes one or more nonpolar structuring agents, one or more emulsifiers, one or more mucoadhesive polymers, and one or more active ingredients effective for providing oral pain relief. The oral care composition can be a solid or semi-solid composition up to a temperature of at least 40° C. Methods of providing such an oral care composition are also provided herein.

20 Claims, No Drawings

ORAL CARE COMPOSITION

CROSS-REFERENCE TO RELATED APPLICATIONS

This application is a national stage filing under 35 U.S.C. 371 of PCT/IB2018/053759, filed May 25, 2018, which International Application was published by the International Bureau in English on Nov. 29, 2018, and application claims priority from U.S. Provisional Application No. 62/511,715, filed on May 26, 2017, which applications are hereby incorporated in their entirety by reference in this application.

FIELD OF THE INVENTION

The present invention relates to oral compositions useful for providing pain relief, and more particularly to a soluble mucoadhesive oral composition.

BACKGROUND

This invention relates to a pliable and soluble mucoadhesive oral composition that is capable of providing targeted and long-lasting delivery of active ingredients for the temporary relief of pain and various oral discomfort ailments including toothaches and mouth sores.

Current solutions for the topical treatment of toothaches and mouth sores are mainly delivered in the form of liquids, pastes, gels, patches, disks and pressed tablets. These forms often dissolve, spread easily, or get dislocated and cause numbness throughout the oral mucosa. Furthermore, the existing compositions generally provide only a short-term analgesic effect.

Accordingly, there is still a desire and a need to provide an oral care composition that enables the active ingredient(s) to be delivered locally to the treatment site through the oral composition in a much more targeted fashion. It is further desirable to provide an oral composition that provides a long-lasting pain relief compared to existing products.

SUMMARY OF THE INVENTION

In one aspect of the present invention, a pliable and soluble mucoadhesive oral composition is provided. The inventive product overcomes the deficiencies of the prior art and enables the active ingredient(s) to be delivered locally to the treatment site through the mucoadhesive oral composition in a much more targeted fashion. When applied at the treatment site, the oral care composition provides a long-lasting pain relief as compared to the existing products. The composition can be a semi-solid dosage form that can be molded when applied to the treatment site so as to provide a "cushion" around the afflicted area. It can provide good adhesion for maximum and targeted delivery of drug and hence, a more gradual coverage and longer duration of relief from pain and various oral discomfort ailments.

The invention includes, without limitation, the following embodiments:

Embodiment 1

An oral care composition comprising one or more nonpolar structuring agents; one or more emulsifiers; one or more mucoadhesive polymers; and one or more active ingredients effective for providing oral pain relief; wherein the oral care composition is a solid or semi-solid composition up to a temperature of at least 40° C.

Embodiment 2

An oral care composition of any preceding embodiment, wherein one or more of the following conditions is met: the one or more nonpolar structuring agents are present in amounts in the range of about 20 to about 35 weight percent, based on the total weight of the oral care composition; the one or more emulsifiers are present in amounts in the range of about 1 to about 5 weight percent, based on the total weight of the oral care composition; the one or more mucoadhesive polymers are present in amounts in the range of about 30 to about 60 weight percent, based on the total weight of the oral care composition.

Embodiment 3

An oral care composition of any preceding embodiment, wherein the one or more structuring agents comprise at least one of a paraffin and a wax.

Embodiment 4

An oral care composition of any preceding embodiment, wherein the one or more structuring agents comprise at least one of petrolatum and beeswax.

Embodiment 5

An oral care composition of any preceding embodiment, wherein the one or more emulsifiers comprise at least one of a polysorbate, an alcohol, hydrogenated castor oil, a vegetable fat, and derivatives thereof.

Embodiment 6

An oral care composition of any preceding embodiment, wherein the one or more emulsifiers comprise at least one of polysorbate 60, cetearyl alcohol, PEG-40 hydrogenated castor oil, and *Theobroma cacao* (cocoa) seed butter.

Embodiment 7

An oral care composition of any preceding embodiment, wherein the one or more mucoadhesive polymers comprise at least one of a cellulosic material, a polyacrylate, and a cellulose derivative.

Embodiment 8

An oral care composition of any preceding embodiment, wherein the one or more mucoadhesive polymers comprise at least one of a cellulose gum and a calcium/sodium PVM/MA copolymer.

Embodiment 9

An oral care composition of any preceding embodiment, wherein the one or more active ingredient comprises at least one of benzocaine and menthol.

Embodiment 10

An oral care composition of any preceding embodiment, further comprising a solubilizing agent.

Embodiment 11

An oral care composition of any preceding embodiment, further comprising a solubilizing agent, wherein the solubilizing agent is polyethylene glycol.

Embodiment 12

An oral care composition of any preceding embodiment, further comprising a solubilizing agent, wherein the solubilizing agent is present in an amount in the range of about 1 to about 5 weight percent, based on the total weight of the oral care composition.

Embodiment 13

An oral care composition of any preceding embodiment, further comprising a flavoring agent.

Embodiment 14

An oral care composition of any preceding embodiment, further comprising a flavoring agent, wherein the flavoring agent is present in an amount in the range of about 0.1 to about 2 weight percent, based on the total weight of the oral care composition.

Embodiment 15

A method of making an oral care composition comprising: forming a premix comprising a solubilizing agent, a sweetener, and a first active ingredient; forming a main batch comprising one or more polar structuring agents, one or more emulsifiers, one or more mucoadhesive polymers, and one or more active ingredients; mixing the premix into the main batch to form the oral care composition; wherein the oral care composition is a solid or semi-solid composition up to a temperature of at least 40° C.

Embodiment 16

The method of any preceding embodiment, wherein the step of forming the premix comprises: adding the sweetener to the solubilizing agent and heating the solubilizing agent and the sweetener to a temperature of about 55-60° C.; vigorously mixing the solubilizing agent and the sweetener until all of the sweetener is dissolved; adding the first active ingredient to the solubilizing agent and the sweetener; and mixing the solubilizing agent, the sweetener, and the first active ingredient until the first active ingredient is dissolved in order to form the premix.

Embodiment 17

The method of any preceding embodiment, wherein the step of forming the main batch comprises: adding the one or more structuring agents and the one or more emulsifiers to a main batch tank; heating the one or more structuring agents and the one or more emulsifiers in the main batch tank to a temperature of about 70-75° C.; mixing the one or more structuring agents and the one or more emulsifiers in the main batch tank until the batch is uniform; adding the one or more active ingredients to the main batch tank; allowing the mixture in the main batch tank to cool to a temperature of about 55-60° C.; adding one or more mucoadhesive polymers to the main batch tank; and mixing the one or more structuring agents, the one or more emulsifiers, the one or more active ingredients, and the one or more mucoadhesive polymers in the main batch tank until the batch is uniform.

Embodiment 18

The method of any preceding embodiment, further comprising adding a flavoring agent to the premix.

Embodiment 19

The method of any preceding embodiment, further comprising carrying out an extrusion and cut process, a hot filled process, or a molded process to provide the oral care composition with one or more of a desired dosage size, shape, and weight.

Embodiment 20

The oral care composition of any preceding embodiment, wherein the oral care composition is manufactured in the form of a final oral care product having a desired dosage size, shape and weight via an extrusion and cut process, a hot filled process, or a molded process.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

DETAILED DESCRIPTION OF THE INVENTION

The present disclosure now will be described more fully hereinafter. The disclosure may be embodied in many different forms and should not be construed as limited to the embodiments set forth herein; rather, these embodiments are provided so that this disclosure will satisfy applicable legal requirements. Like numbers refer to like elements throughout. As used in this specification and the claims, the singular forms "a," "an," and "the" include plural references unless the context clearly dictates otherwise.

In one aspect of the present invention, an oral care composition is provided comprising one or more structuring agents, one or more emulsifiers, one or more mucoadhesive polymers, and one or more active ingredients effective for providing oral pain relief, wherein the oral care composition is a solid or semi-solid composition which can remain in its positioned location for an extended period of time, and which dissolves in saliva very slowly due to its unique composition. The main advantages of the invention include a more targeted/localized and longer duration of numbing pain relief in the form of a pliable mucoadhesive semi-solid. The invention also provides a more soothing and comfortable experience via its dough-like consistency that allows the user to easily customize and mold it around the treatment site so as to provide a "cushion" around the afflicted area.

The one or more structuring agents can help in the slow dissolution of the oral care composition in the oral cavity, thereby increasing the duration of pain relief provided to the user. In various embodiments, the one or more structuring agents can comprise a nonpolar material. As non-limiting examples, the one or more structuring agents can comprise at least one of a paraffin and a wax. More particularly, the one or more structuring agents can comprise at least one of petrolatum and beeswax. In certain embodiments, a wax (e.g., beeswax) can enhance the malleability of the oral care composition so as to allow the user to easily mold it to the application site and provide a soothing and comforting experience. The wax can further provide a firmness to the oral care composition. In certain embodiments, a paraffin can provide smoothness and malleability to the oral care composition.

It is noted that the inventive product provides pain relief for a longer duration (up to 90 to 120 minutes) in comparison to currently available products such as Anbesol and Orajel (typically 5 to 15 minutes). Both of these products for pain relief are relatively short acting. While it is desirable for the oral composition to be dissolvable within the mouth, the oral composition must persist in the mouth for a sufficient time to provide a useful effect. Without being limited by theory, one of the probable reasons for the insufficient effective time of known products for oral pain relieve is that such known products contain primarily polar ingredients that are more readily soluble in the oral mucosa which influences the duration of pain relief offered. In the case of the inventive product, the use of a primarily nonpolar base provides a slow dissolution and hence, long lasting effect. Preferably, the present oral composition dissolves within the mouth and provides a pain-relieving effect for a time of at least 15 minutes, at least 30 minutes, or at least 45 minutes (e.g., up to a time of about 4 hours). In some embodiments, the present oral composition dissolves within the mouth and provides a pain-relieving effect for a time of about 20 minutes to about 180 minutes, about 30 minutes to about 150 minutes, or about 45 minutes to about 120 minutes.

In certain embodiments, the one or more nonpolar structuring agents can be present in amounts in the range of about 15 to about 50 weight percent, about 20 to about 40 weight percent, or about 25 to about 35 weight percent, based on the total weight of the oral care composition. In certain embodiments, the one or more nonpolar structuring agents can be present in an amount of at least about 15 weight percent, at least about 20 weight percent, or at least about 25 weight percent, based on the total weight of the oral care composition (e.g., with a maximum concentration of about 60 percent by weight).

The use of an emulsifying mixture can help breakdown the mostly nonpolar composition base provided by the structuring agents and provide a more controlled release of active ingredient(s) into the treatment site. In various embodiments, the oral care composition can comprise one or more emulsifiers selected from the group consisting of polysorbates, alcohols, hydrogenated castor oils, vegetable fats, derivatives thereof, and combinations thereof. For example, the one or more emulsifiers comprise at least one of polysorbate 60, cetearyl alcohol, PEG-40 hydrogenated castor oil, and *Theobroma cacao* (cocoa) seed butter.

In various embodiments, the one or more emulsifiers can be present in amounts in the range of about 0.5 to about 15 weight percent, about 1 to about 10 weight percent, or about 2 to about 5 weight percent, based on the total weight of the oral care composition. In certain embodiments, the one or more emulsifiers can be present in an amount of at least about 1 weight percent, or at least about 3 weight percent, based on the total weight of the oral care composition (e.g., up to a maximum concentration of about 20 weight percent).

The use of a mucoadhesive polymer blend can provide an improvement in the adhesive characteristics of the oral care composition to the oral mucosa. In various embodiments, the one or more mucoadhesive polymers can comprise at least one of a cellulosic material, a polyacrylate, and one or more cellulose derivatives. For example, the one or more mucoadhesive polymers can comprise at least one of a cellulose gum and a calcium/sodium PVM/MA copolymer. In certain embodiments, at least two different mucoadhesive polymers can be used to provide the desired adhesion. For example, a first mucoadhesive polymer can be used to provide an initial, immediate adhesion (e.g., adhesion within a time of about 1 second to about 30 seconds) to provide the initial immediate adhesion needed to ensure the product (especially in its semi-solid form) adheres quickly to the oral mucosa and stays on the application site. A cellulose gum is an example of a mucoadhesive polymer that can provide such effect. As a further example, a second, different mucoadhesive polymer can be used to provide the desired longer-lasting adhesion (e.g., beyond a time of about 15 minutes) lacking in current market gel and cream forms that spread throughout and dissipate quickly in the oral cavity. A calcium/sodium PVM/MA copolymer or similar compound can provide such effect.

In various embodiments, the one or more mucoadhesive polymers can be present in amounts in the range of about 20 to about 75 weight percent, about 30 to about 60 weight percent, or about 40 to about 50 weight percent, based on the total weight of the oral care composition. In certain embodiments, the one or more mucoadhesive polymers can be present in an amount of at least about 25 weight percent, at least about 30 weight percent, or at least about 40 weight percent, based on the total weight of the oral care composition (e.g., with a maximum concentration of about 75 weight percent).

In various embodiments, one or more active ingredients can be included in the oral care composition to provide pain relief and/or soothing and cooling effects of the product. The one or more active ingredients can be present in an amount suitable for providing oral pain relief. For example, menthol can be used in the oral care composition to provide additional pain relief specifically to the gums via the cooling effect of the active ingredient. Menthol can be present in an amount of, for example, about 0.01 to about 3 weight percent, based on the total weight of the oral care composition. In various embodiments, benzocaine can be included in the oral care composition to provide pain relief to the treatment area. The benzocaine can be present in an amount of, for example, about 5 to about 30, or about 10 to about 25 weight percent, or about 15 to about 20 weight percent, based on the total weight of the oral care composition. Other active ingredients known in the art can be added to the oral care product as desired. Moreover, the total amount of active ingredient(s) present in the oral care composition can vary based on the type of active ingredient(s) used and/or the number of different active ingredients used.

In various embodiments, the oral care composition can further comprise at least one solubilizing agent. For example, the oral care composition can comprise polyethylene glycol (PEG). In certain embodiments, the solubilizing agent can be present in an amount in the range of about 1 to about 5 weight percent, or about 2 to about 3 weight percent, based on the total weight of the oral care composition. In certain embodiments, the one or more solubilizing agents can be present in an amount of at least about 1 weight percent, or at least about 2 weight percent, based on the total weight of the oral care composition. In some embodiments, it can be desirable to limit the amount of PEG that is present in the composition. For example, the present oral care composition may comprise no greater than 10 weight percent, no greater than 5 weight percent, or no greater than 2 weight percent. In some embodiments, the present oral care composition can be free of PEG beyond a trace amount (e.g., less than 0.1 weight percent or less than 0.01 weight percent).

In various embodiments, the oral care composition can further comprise one or more additional ingredients. For example, the oral care composition can comprise at least one of a sweetener and a flavoring agent. In some embodiments, a sweetener can be present in an amount in the range of about 0.1 to about 1 weight percent, or about 0.2 to about 0.5 weight percent, based on the total weight of the oral care composition. In various embodiments, a sweetener can be present in an amount of at least about 0.1 weight percent, based on the total weight of the oral care composition (e.g., with a maximum concentration of about 10 weight percent). In some embodiments, a flavoring agent can be present in an amount in the range of about 0.1 to about 2 weight percent, or about 0.5 to about 1 weight percent, based on the total weight of the oral care composition. The flavoring agent can be present in an amount of at least about 0.1 weight percent, or at least about 0.5 weight percent, based on the total weigh of the oral care composition (e.g., with a maximum concentration of about 10 weight percent).

In various embodiments of the present invention, the oral care composition is in a malleable form (i.e., the composition maintains a dough-like consistency and does not crumble or fall apart when applying and molding to a treatment site), and is easily manipulated and can be put into place using the user's fingers. The inventive product provides a targeted and localized delivery of action for the duration of treatment, is soluble in oral mucosa, and can be present as a solid or semisolid formulation. The formulated composition easily adheres to the tooth and gum, thereby, providing a maximum level of active ingredient (e.g., benzocaine) to be delivered at the treatment site to provide immediate relief. In addition, the adhesive properties of the present invention allow for the product to stay in play while a user is talking and/or drinking.

Furthermore, embodiments of the present invention provide a comparatively long lasting effect as described above and thus overcome all the deficiencies associated with conventional oral treatment compositions. For example, in the presence of saliva, certain embodiments of the oral care composition can remain in a semi-solid or solid state for at least about 5 minutes, at least about 20 minutes, at least about 30 minutes, at least about 60 minutes, at least about 90 minutes, or at least about 120 minutes. In certain embodiments, the oral care composition can remain in a semi-solid or solid state when in the oral cavity for about 60 to about 120 minutes. The inventive product is a single application product with a measured dose. Its long-lasting pain relief benefit also helps to reduce the need for frequent reapplication and helps reduce the need to intake additional oral analgesics such as Tylenol and Advil.

A method of making an oral care composition is also provided herein. In various embodiments, the method can comprise first making a premix which can then be added to the main batch. The premix can be formed by mixing a solubilizing agent and, if desired, a sweetener and/or flavoring agent until the mixture is uniform and the sweetener and/or flavoring agent are dissolved. This mixing process can be performed at a temperature of about 40-60° C., for example. In certain embodiments, just before the premix is added to the main batch, Menthol can be added to the premix and the mixture can be mixed until the Menthol dissolves. The temperature of the premix can be maintained at a temperature of about 40-60° C. In the main batch tank, one or more nonpolar structuring agents and one or more emulsifiers can each be added to the tank. The mixture of one or more nonpolar structuring agents and one or more emulsifiers can be mixed and heated to a temperature of about 60-75° C. Once the batch is uniform, at least one active ingredient (e.g., Benzocaine) can be added to the main batch. The temperature of the main batch can then be allowed to cool to about 40-60° C., for example. Next, one or more mucoadhesive polymers can be added to the cooled main batch. The temperature of the main batch can be maintained at about 40-60° C. while the ingredients are mixed until the batch is uniform. Finally, the premix can be added to the main batch. Again, the temperature of the final mixture can be maintained at about 40-60° C. while the ingredients are mixed until the batch is uniform. The final product can then be either extruded or hot filled, and be allowed to cool to room temperature. Example 1 below provides a detailed method of making an embodiment of the oral care compositions disclosed herein.

EXAMPLES

Example 1

An embodiment of an oral care composition (referred to as "Formula 1") is provided and a method of making the same. Table 1 below provides ingredients included in an embodiment of the oral care composition of the present invention. The ingredients are listed by order of addition, as described in more detail below. Table 1 also includes the weight percentage of each ingredient, based on the total weight of the oral care composition. The primary function of each ingredient is also included.

TABLE 1

Oral Care Composition Formula 1

| Batch | Ingredient | Function | Weight Percentage |
|---|---|---|---|
| Premix | Polyethylene Glycol | Solubilizing Agent | 1-5 wt. % |
| Premix | Sucralose | Sweetener | 0.1-2 wt. % |
| Premix | Menthol | Active Ingredient | 0.01-2 wt. % |
| Premix | Methyl Salicylate | Flavoring Agent | 0.1-2 wt. % |
| Main | Petrolatum | Structuring Agent | 15-30 wt. % |
| Main | Beeswax | Structuring Agent | 5-20 wt. % |
| Main | Cetearyl Alcohol (and) Polysorbate 60 | Emulsifier | 0.1-5 wt. % |
| Main | PEG-40 Hydrogenated Castor Oil | Emulsifier | 1-5 wt. % |
| Main | Theobroma Cacao (Cocoa) Seed Butter | Emulsifier | 1-5 wt. % |
| Main | Benzocaine | Active Ingredient | 5-20 wt. % |
| Main | Calcium/Sodium PVM/MA Copolymer | Mucoadhesive Polymer | 15-30 wt. % |
| Main | Cellulose Gum | Mucoadhesive Polymer | 15-30 wt. % |

First a premix was prepared. The polyethylene glycol was added to a tank and vigorously mixed as the sucralose was added. This mixture was heated to a temperature of about 55-60° C. and mixed until all of the sucralose was dissolved. The mixture was then held at a temperature of about 55-60° C. Just before the premix was added to the main batch, the menthol was added to the premix and mixed until dissolved. The temperature was maintained a temperature of about 55-60° C. Next the methyl salicylate was added to the premix and mixed until uniform, again maintaining a temperature of about 55-60° C.

The main batch was prepared by adding the premelted petrolatum, the beeswax, the cetearyl alcohol (and) polysorbate 60, the PEG-40 hydrogenated castor oil, and the *Theobroma cacao* (cocoa) seed butter to the main batch tank. This mixture was mixed using a sweep agitation, ribbon blender, or plough mixer process and heated to a temperature of about 70-75° C. When all the beeswax was melted and the batch was uniform, the benzocaine was added to the main batch and the main batch was then cooled to a temperature of about 55-60° C. Next, the calcium/sodium PVM/MA copolymer was added and a temperature of about 55-60° C. was maintained. The cellulose gum was then added and again a temperature of about 55-60° C. was maintained. The main batch mixture was then mixed until it was uniform, approximately 30 minutes. Finally, the premix was added to the main batch and this final composition was mixed until uniform (approximately 120 minutes minimum) at a temperature of about 55-60° C.

Once the final oral composition was formed, it was extruded at a temperature of about 55-60° C., cut to the desired application size and shape, and dusted with cellulose gum powder or silica powder in order to prevent the cut extrudes from sticking to themselves.

Example 2

A final oral composition was formed according to Example 1 above. However, as an alternative, the heated product can alternatively be hot filled into a mold, a tube, or a section packaging tray at the proper weight prior to cooling and sealing to provide the correct dose size and shape.

Example 3

For comparative purposes, an oral care composition (hereinafter referred to as "Formula 2") that was mainly PEG-based and did not include any mucoadhesives was prepared. The ingredients are listed in Table 2 by order of addition. A process similar to the process described in Example 1 above was used to prepare Formula 2. Table 2 also includes the weight percentage of each ingredient, based on the total weight of the oral care composition. The primary function of each ingredient is also included.

TABLE 2

Oral Care Composition Formula 2

| Batch | Ingredient | Function | Weight Percentage |
|---|---|---|---|
| Premix | Polyethylene Glycol | Solubilizing Agent | 15-30 wt. % |
| Premix | PEG-2M | Adhesive/Binder | 1-5 wt. % |
| Main | Polyethylene Glycol | Solubilizing Agent | 50-70 wt. % |
| Main | Cetyl Alcohol | Structuring Agent | 1-10 wt. % |
| Main | Sodium Saccharin USP | Sweetener | 0.1-2 wt. % |
| Main | Benzocaine | Active Ingredient | 5-20 wt. % |
| Main | Flavor | Flavoring Agent | 0.1-2 wt. % |

The premix was formed by mixing the polyethylene glycol (e.g., Carbowax Sentry PEG 400 NF, FCC Grade) with the PEG-2M (e.g., Sentry Polyox WSR N10-LEO NF Grade). In the main mixture, the polyethylene glycol (e.g., Carbowax Sentry PEG 3350 Granular NF, FCC Grade) and the cetyl alcohol were mixed followed by the sodium saccharin, benzocaine, premix, and flavor (e.g., N&A *Eucalyptus* Mint Flavor).

Example 4

A qualitative test with focus groups was conducted with Formula 1 (prepared according to Example 1 above). 28 adults who had used topical toothache medication in the past six months were asked to use the products at the testing facility and to then comment on their experience in groups. Based on the feedback received from the focus groups, several conclusions were drawn, as listed below.

1. Formula 1 (the inventive product) is found to be soothing and comfortable to the applicant.
2. Besides delivering pain relieving medication, Formula 1 also provides a soft comfortable cushion for the aching tooth or mouth sore. This creates an advantageous difference of Formula 1 over other topical analgesics used for dental or mouth pain.
3. Currently used products produce numbness over the entire mouth, tongue and throat due to their dislocation from the point of application and/or excessive dripping. Formula 1 remedies those issues by staying in one place and producing stronger numbness in the application area with minimal numbing in other areas.
4. Formula 1 offers longer-lasting relief in comparison to other prevalent products in just one application.
5. Also, the semi-solid form allows the Formula 1 product to be easily molded and applied over the pain area. The formulated "cushion" easily adheres to the tooth and gum, thereby, providing immediate relief and the maximum level of analgesic active ingredient to be delivered to the toothache site.
6. The Formula 1 product provides long acting relief up to 90 to 120 minutes and is quite long lasting particularly compared to what is usually experienced with the current market products.
7. The light mint flavor of the Formula 1 product results in a pleasant taste that is more appealing and acceptable than most current market products.
8. The Formula 1 product is thought to have an acceptable level of numbing for the length of relief provided.
9. The Formula 1 product has improved adhesion to the oral mucosa, improved product malleability, and better controlled release than current market products.

Many modifications and other embodiments of the disclosure will come to mind to one skilled in the art to which this disclosure pertains having the benefit of the teachings presented in the foregoing description; and it will be apparent to those skilled in the art that variations and modifications of the present disclosure can be made without departing from the scope or spirit of the disclosure. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:
1. An oral care composition comprising:
one or more nonpolar structuring agents;
one or more emulsifiers;
one or more mucoadhesive polymers; and
one or more active ingredients effective for providing oral pain relief;

wherein the oral care composition is a solid or semi-solid composition up to a temperature of at least 40° C.; and
wherein the oral care composition is in a dosage form that is malleable and moldable and has a dough-like consistency.

2. The oral care composition of claim 1, wherein one or more of the following conditions is met:
the one or more nonpolar structuring agents are present in amounts in the range of about 20 to about 35 weight percent, based on the total weight of the oral care composition;
the one or more emulsifiers are present in amounts in the range of about 1 to about 5 weight percent, based on the total weight of the oral care composition;
the one or more mucoadhesive polymers are present in amounts in the range of about 30 to about 60 weight percent, based on the total weight of the oral care composition.

3. The oral care composition of claim 1, wherein the one or more structuring agents comprise at least one of a paraffin and a wax.

4. The oral care composition of claim 1, wherein the one or more structuring agents comprise at least one of petrolatum and beeswax.

5. The oral care composition of claim 1, wherein the one or more emulsifiers comprise at least one of a polysorbate, an alcohol, hydrogenated castor oil, a vegetable fat, and derivatives thereof.

6. The oral care composition of claim 1, wherein the one or more emulsifiers comprise at least one of polysorbate 60, cetearyl alcohol, PEG-40 hydrogenated castor oil, and Theobroma cacao (cocoa) seed butter.

7. The oral care composition of claim 1, wherein the one or more mucoadhesive polymers comprise at least one of a cellulosic material, a polyacrylate, and a cellulose derivative.

8. The oral care composition of claim 1, wherein the one or more mucoadhesive polymers comprise at least one of a cellulose gum and a calcium/sodium PVM/MA copolymer.

9. The oral care composition of claim 1, wherein the one or more active ingredient comprises at least one of benzocaine and menthol.

10. The oral care composition of claim 1, further comprising a solubilizing agent.

11. The oral care composition of claim 10, wherein the solubilizing agent is polyethylene glycol.

12. The oral care composition of claim 10, wherein the solubilizing agent is present in an amount in the range of about 1 to about 5 weight percent, based on the total weight of the oral care composition.

13. The oral care composition of claim 1, further comprising a flavoring agent.

14. The oral care composition of claim 13, wherein the flavoring agent is present in an amount in the range of about 0.1 to about 2 weight percent, based on the total weight of the oral care composition.

15. The oral care composition of claim 1, wherein the oral care composition is manufactured in the form of a final oral care product having a desired dosage size, shape and weight via an extrusion and cut process, a hot filled process, or a molded process.

16. The oral care composition of claim 1, wherein the one or more structuring agents comprise both a paraffin and a wax.

17. The oral care composition of claim 1, wherein the one or more emulsifiers comprise both a hydrogenated castor oil and a vegetable fat.

18. The oral care composition of claim 1, wherein the one or more mucoadhesive polymers includes a calcium/sodium PVM/MA copolymer.

19. The oral care composition of claim 1, wherein the one or more structuring agents comprise both petrolatum and beeswax.

20. The oral care composition of claim 1, wherein the one or more active ingredients comprise both benzocaine and menthol.

* * * * *